US011589627B2

(12) United States Patent
Sorrels

(10) Patent No.: US 11,589,627 B2
(45) Date of Patent: Feb. 28, 2023

(54) PROTECTIVE GLOVES AND METHOD OF MAKING PROTECTIVE GLOVES

(71) Applicant: Protospheric Products, Inc., Clearwater, FL (US)

(72) Inventor: Kevin Sorrels, Clearwater, FL (US)

(73) Assignee: Protospheric Products, Inc., Clearwater, FL (US)

( * ) Notice: Subject to any disclaimer, the term of this patent is extended or adjusted under 35 U.S.C. 154(b) by 308 days.

(21) Appl. No.: 16/331,238

(22) PCT Filed: Sep. 11, 2017

(86) PCT No.: PCT/US2017/050890
§ 371 (c)(1),
(2) Date: Mar. 7, 2019

(87) PCT Pub. No.: WO2018/049297
PCT Pub. Date: Mar. 15, 2018

(65) Prior Publication Data
US 2019/0183193 A1    Jun. 20, 2019

Related U.S. Application Data

(60) Provisional application No. 62/385,526, filed on Sep. 9, 2016.

(51) Int. Cl.
*A41D 19/00* (2006.01)
*A41D 19/015* (2006.01)
(Continued)

(52) U.S. Cl.
CPC ..... *A41D 19/0068* (2013.01); *A41D 19/0006* (2013.01); *A41D 19/0058* (2013.01);
(Continued)

(58) Field of Classification Search
CPC ............ A41D 19/0068; A41D 19/0006; A41D 19/0058; A41D 19/015; A41D 19/0096; A41D 2500/50; A41D 31/24; A41D 31/245; A41D 2300/52; A61B 42/00; A61B 42/10; A61B 42/20; B32B 2437/02; B32B 1/00; B32B 27/08; B32B 27/32; B32B 27/40;
(Continued)

(56) References Cited

U.S. PATENT DOCUMENTS 133,640 A    3/1873 Bond
1,316,292 A    9/1919 Fleming
(Continued)

FOREIGN PATENT DOCUMENTS

CN    204070672    1/2015

OTHER PUBLICATIONS

International Search Report and Written Opinion for PCT Application No. PCT/US2017/050890 dated Nov. 29, 2017.
(Continued)

*Primary Examiner* — Catherine A. Simone
(74) *Attorney, Agent, or Firm* — Mark R. DeLuca; Womble Bond Dickinson (US) LLP

(57) ABSTRACT

A protective guard for a hand, finger or thumb includes a first thermoplastic layer heat welded to second thermoplastic layer. The second thermoplastic layer has a thickness that is greater than the thickness of the first thermoplastic layer.

9 Claims, 2 Drawing Sheets

(51) Int. Cl.
  *A61B 42/20* (2016.01)
  *A61B 42/00* (2016.01)
  *A61B 42/10* (2016.01)
  *B29C 65/00* (2006.01)
  *B29C 65/18* (2006.01)
  *A44B 11/25* (2006.01)
  *B29C 65/74* (2006.01)
  *B29L 31/48* (2006.01)
  *B29C 65/04* (2006.01)
  *B29C 65/02* (2006.01)
  *B29C 65/08* (2006.01)

(52) U.S. Cl.
  CPC ....... *A41D 19/0096* (2013.01); *A41D 19/015* (2013.01); *A44B 11/2546* (2013.01); *A61B 42/00* (2016.02); *A61B 42/10* (2016.02); *A61B 42/20* (2016.02); *B29C 65/18* (2013.01); *B29C 65/7435* (2013.01); *B29C 65/7441* (2013.01); *B29C 65/7455* (2013.01); *B29C 66/1122* (2013.01); *B29C 66/244* (2013.01); *B29C 66/4326* (2013.01); *B29C 66/73921* (2013.01); *B29C 66/83411* (2013.01); *B29C 66/83511* (2013.01); *B29C 66/91411* (2013.01); *B29C 66/91421* (2013.01); *B29C 66/91943* (2013.01); *A41D 2500/50* (2013.01); *B29C 65/02* (2013.01); *B29C 65/04* (2013.01); *B29C 65/08* (2013.01); *B29C 66/71* (2013.01); *B29C 66/712* (2013.01); *B29C 66/723* (2013.01); *B29C 66/73152* (2013.01); *B29C 66/73521* (2013.01); *B29C 66/8122* (2013.01); *B29L 2031/4864* (2013.01)

(58) Field of Classification Search
  CPC . A44B 11/2546; B29C 65/18; B29C 65/7435; B29C 65/7441; B29C 65/7455; B29C 65/02; B29C 65/04; B29C 65/08; B29C 66/71; B29C 66/712; B29C 66/723; B29C 66/73152; B29C 66/73521; B29C 66/8122; B29C 66/1122; B29C 66/244; B29C 66/4326; B29C 66/73921; B29C 66/83411; B29C 66/83511; B29C 66/91411; B29C 66/91943
  See application file for complete search history.

(56) References Cited

U.S. PATENT DOCUMENTS

| | | | |
|---|---|---|---|
| 1,337,957 | A | 4/1920 | Rasmussen |
| 1,388,618 | A | 8/1921 | Stein et al. |
| 2,379,624 | A | 7/1945 | Chisnell |
| 2,538,889 | A | 1/1951 | Swairin |
| 2,935,354 | A | 5/1960 | Chapman |
| 3,070,804 | A | 1/1963 | Parrilla |
| 3,228,033 | A | 1/1966 | Ames et al. |
| 3,681,784 | A * | 8/1972 | Lindley ............ A41D 19/0068 2/162 |
| 3,728,736 | A | 4/1973 | Pugh |
| 4,034,853 | A | 7/1977 | Smith |
| 4,127,222 | A | 11/1978 | Adams |
| 4,433,439 | A | 2/1984 | Sidman et al. |
| 4,689,828 | A | 9/1987 | Brewer |
| 4,694,843 | A | 9/1987 | Casenhiser |
| 4,796,302 | A | 1/1989 | Davis et al. |
| 4,858,245 | A | 8/1989 | Sullivan et al. |
| 4,901,372 | A | 2/1990 | Pierce |
| 4,958,384 | A | 9/1990 | McCrane |
| 4,985,038 | A | 1/1991 | Lyell |
| 5,070,543 | A | 12/1991 | Beck |
| 5,133,087 | A | 7/1992 | Machida et al. |
| 5,231,700 | A | 8/1993 | Cutshall |
| 5,421,033 | A | 6/1995 | Deleo |
| 5,450,626 | A | 9/1995 | Sorrels |
| D373,656 | S | 9/1996 | Sorrels |
| 5,685,014 | A | 11/1997 | Dapsalmon |
| 5,833,915 | A | 11/1998 | Shah |
| 5,842,227 | A | 12/1998 | Rabin et al. |
| 5,864,885 | A | 2/1999 | Grinberg |
| 5,924,428 | A | 7/1999 | Song |
| 5,953,752 | A | 9/1999 | Jones |
| 6,021,523 | A | 2/2000 | Vero |
| 6,035,444 | A | 3/2000 | McGrew |
| 6,052,829 | A | 4/2000 | Kindler |
| RE36,778 | E | 7/2000 | Deleo |
| 6,081,927 | A | 7/2000 | Gimbel |
| 6,094,748 | A | 8/2000 | Kindler |
| 6,111,233 | A | 8/2000 | Rock et al. |
| 6,115,850 | A | 9/2000 | Grilliot et al. |
| 6,141,801 | A | 11/2000 | Helenick |
| 6,154,886 | A | 12/2000 | Hottner |
| 6,230,524 | B1 | 5/2001 | Kolmes et al. |
| 6,235,340 | B1 | 5/2001 | Lee et al. |
| 6,237,148 | B1 | 5/2001 | Graham |
| 6,254,988 | B1 | 7/2001 | Zhu et al. |
| 6,260,344 | B1 | 7/2001 | Chakravarti |
| 6,266,951 | B1 | 7/2001 | Chakravarti |
| 6,272,687 | B1 | 8/2001 | Cunningham |
| 6,298,488 | B1 | 10/2001 | Duncan et al. |
| 6,301,715 | B1 | 10/2001 | Hoffmann |
| 6,338,162 | B1 | 1/2002 | Geng |
| 6,341,483 | B1 | 1/2002 | Kolmes et al. |
| 6,345,394 | B1 | 2/2002 | Nakamura et al. |
| 6,349,531 | B1 | 2/2002 | Kolmes et al. |
| 6,351,932 | B1 | 3/2002 | Hummel |
| 6,363,703 | B1 | 4/2002 | Kolmes |
| 6,367,290 | B2 | 4/2002 | Kolmes et al. |
| 6,374,417 | B1 | 4/2002 | Stagnitta |
| 6,381,940 | B1 | 5/2002 | Kolmes et al. |
| 6,383,614 | B1 | 5/2002 | Carson et al. |
| 6,415,446 | B1 | 7/2002 | McLean et al. |
| 6,457,182 | B1 | 10/2002 | Szczesuil et al. |
| 6,460,192 | B2 | 10/2002 | Kindler |
| 6,467,251 | B1 | 10/2002 | Kolmes |
| 6,468,646 | B2 | 10/2002 | Carson et al. |
| 6,516,469 | B1 | 2/2003 | Schaetzel |
| 6,517,659 | B1 | 2/2003 | VanderWerf et al. |
| 6,526,592 | B1 | 3/2003 | Best |
| 6,543,059 | B2 | 4/2003 | Szczesuil et al. |
| 6,548,789 | B1 | 4/2003 | Rock et al. |
| 6,581,366 | B1 | 6/2003 | Andrews |
| 6,591,427 | B1 | 7/2003 | Bennett |
| 6,640,341 | B1 | 11/2003 | Calvert |
| 6,647,549 | B2 | 11/2003 | McDevitt et al. |
| 6,696,128 | B2 | 2/2004 | McIntee et al. |
| 6,721,987 | B2 | 4/2004 | McDevitt et al. |
| 6,760,924 | B2 | 7/2004 | Hatch et al. |
| 6,800,234 | B2 | 10/2004 | Ferguson et al. |
| 6,807,681 | B2 | 10/2004 | Sorrels |
| 6,829,881 | B1 | 12/2004 | Manten |
| 6,874,336 | B2 | 4/2005 | Yarborough et al. |
| 6,911,247 | B2 | 6/2005 | Howland |
| 6,928,658 | B2 | 8/2005 | Taira et al. |
| 6,946,182 | B1 | 9/2005 | Allgeuer et al. |
| 6,962,739 | B1 | 11/2005 | Kim et al. |
| 7,007,308 | B1 | 3/2006 | Howland et al. |
| 7,018,692 | B2 | 3/2006 | Kim et al. |
| 7,025,851 | B2 | 4/2006 | Caster et al. |
| 7,043,770 | B1 | 5/2006 | Cunningham |
| 7,055,177 | B2 | 6/2006 | Svrcek |
| 7,086,093 | B2 | 8/2006 | Carey et al. |
| 7,100,212 | B2 | 9/2006 | Jaeger |
| 7,100,352 | B2 | 9/2006 | Robins |
| 7,117,540 | B2 | 10/2006 | Morrow |
| 7,200,870 | B1 | 4/2007 | Kolk |
| 7,246,382 | B2 | 7/2007 | Plut et al. |
| 7,284,283 | B2 | 10/2007 | Mack et al. |
| 7,294,678 | B2 | 11/2007 | McGlothin et al. |
| 7,383,590 | B1 | 6/2008 | Duncan |
| 7,320,145 | B2 | 11/2008 | Hochmuth |
| 7,451,496 | B2 | 11/2008 | Carey et al. |

(56) References Cited

U.S. PATENT DOCUMENTS

| | | | |
|---|---|---|---|
| 7,469,427 B2 | 12/2008 | Yang et al. | |
| 7,475,433 B2 | 1/2009 | Coulter et al. | |
| 7,578,004 B2 | 8/2009 | Loyens et al. | |
| 7,669,442 B1 | 3/2010 | Zhu | |
| 7,895,768 B2 | 3/2011 | Vossoughi et al. | |
| 7,932,192 B2 | 4/2011 | Fujisawa et al. | |
| 7,934,395 B2 | 5/2011 | Zhu | |
| 7,934,396 B2 | 5/2011 | Zhu | |
| 8,001,999 B2 | 8/2011 | Schultz | |
| 8,771,820 B1 | 7/2014 | Goodspeed | |
| 8,789,394 B2 | 7/2014 | Tatsumi et al. | |
| 8,863,317 B2 | 10/2014 | Tsuru et al. | |
| 9,029,817 B2 | 5/2015 | Larmigny et al. | |
| D741,551 S | 10/2015 | Piotrowski | |
| 9,161,579 B1 | 10/2015 | Johnson | |
| 9,345,278 B2 | 5/2016 | Crear et al. | |
| 2002/0134392 A1 | 9/2002 | Sorrels | |
| 2002/0184695 A1* | 12/2002 | Fowler | A41D 13/087 2/159 |
| 2003/0150041 A1* | 8/2003 | Patel | A41D 31/04 2/16 |
| 2013/0104286 A1 | 5/2013 | Shawver et al. | |
| 2013/0291282 A1* | 11/2013 | Anstey | A41D 19/00 2/161.7 |
| 2014/0000006 A1 | 1/2014 | Perera et al. | |
| 2014/0005616 A1 | 1/2014 | Moreland et al. | |
| 2014/0026290 A1 | 1/2014 | Howland | |
| 2014/0053854 A1 | 2/2014 | Barry, Jr. | |
| 2014/0059739 A1 | 3/2014 | Gellis | |
| 2014/0075639 A1 | 3/2014 | Albertyn | |
| 2014/0109290 A1 | 4/2014 | Ghazaly et al. | |
| 2014/0157832 A1 | 6/2014 | Thompson et al. | |
| 2014/0259285 A1 | 9/2014 | Andrews et al. | |
| 2014/0283559 A1 | 9/2014 | Andrews et al. | |
| 2015/0047097 A1 | 2/2015 | Tao | |
| 2015/0059043 A1 | 3/2015 | Dwyer | |
| 2015/0164159 A1 | 6/2015 | Hull | |
| 2015/0181955 A1 | 7/2015 | Hughes et al. | |
| 2015/0181956 A1 | 7/2015 | Andrews et al. | |
| 2015/0220146 A1 | 8/2015 | Fisher et al. | |
| 2016/0073713 A1 | 3/2016 | Takata | |
| 2016/0122942 A1 | 5/2016 | Quaresma Ribeiro Campos et al. | |

OTHER PUBLICATIONS

International Preliminary Report on Patentability for PCT Application No. PCT/US2017/050890 dated Mar. 12, 2019.
Chinese Office Action for Chinese Counterpart Application No. 2017800546559 dated Jul. 6, 2020.
Extended European Search Report for European Counterpart Application No. 17849701.2 dated Jul. 21, 2020.
Russian Office Action for Russian Counterpart Application No. 2019104576/03 (008663) dated Mar. 15, 2021.

* cited by examiner

PROTECTIVE GLOVES AND METHOD OF MAKING PROTECTIVE GLOVES

BACKGROUND OF THE INVENTION

1. Field of the Invention

This invention relates generally to protective guards, and specific embodiments relate to protective guards that inhibit skin penetration by sharps.

2. Description of Related Art

Medical practitioners including, but not limited to, doctors, physician assistants, nurses, dentists, and dental assistants may use instruments, implants, and/or needles during medical procedures. Medical procedures may include, but are not limited to, surgical procedures and operations, dental procedures and operations, and injection or drawing of fluids using needles. A risk exists that a medical practitioner's skin may be punctured or penetrated during a medical procedure, resulting in a percutaneous injury. A medical practitioner's skin may also be punctured or penetrated during disposal or cleaning of needles or medical instruments previously used in a medical procedure. The medical practitioner and/or patient may be subject to infection or disease including, but not limited to, staphylococcus, hepatitis, and acquired immunodeficiency syndrome (AIDS) due to an inadvertent skin puncture of the medical practitioner. With or without transmission of a disease or pathogen, a skin puncture or other wound may be traumatic to the medical practitioner. There is a need to protect medical practitioners and patients from the risk of infection and pathogens due to skin punctures or wounds of the medical practitioner during a medical procedure.

Surgical gloves may be used by medical practitioners to lessen the risk of transferring blood-borne and other pathogens during medical procedures. Surgical gloves, however, typically do not provide adequate protection from penetration of skin by sharps. Sharps may include, but are not limited to, hypodermic needles; medical, dental and laboratory instruments (such as scalpels); and burs and sharp edges or projections of hard tissue and prostheses. Studies show that puncture wounds of medical practitioners often occur on backs of a medical practitioner's fingers or thumb. Puncture wounds may occur predominantly to the index finger, thumb, and middle finger. For example, a medical practitioner may hold a syringe in a dominant hand while stabilizing, retracting, isolating, or palpating tissue with the other hand. A sudden movement by the patient may cause the medical practitioner to accidentally puncture the back of a finger or thumb of the non-dominant hand.

Cut and/or puncture resistant gloves are useful in other industries. Protective gloves are used in the food service industry, wherein the glove is intended to act as a protective barrier for food contact. However, many food preparation workers also could benefit from having a glove that protects the worker's hands from cutting utensils. In cosmetology application, barbers and hair salons use gloves to protect the worker's hands from various chemicals such as dyes and bleaches used to color hair. Many cosmetologist could also benefit from a glove that offers protection from accidental scissor cuts and hair splinters. Finally, a cut resistant glove would be useful as a garden glove, a mechanics glove, a sportsman's glove, an all-purpose glove, and a kitchen glove. While there are existing cut/puncture resistant gloves in many of these industries, such gloves tend to be bulky, making it difficult for the user to work.

U.S. Pat. No. 5,450,626 issued to Sorrels, which is incorporated by reference as if fully set forth herein, discloses protective finger coverings that have flexible and puncture resistant construction. A finger covering may include a puncture resistant, protective surface on a top side of the covering, which fits over a dorsal portion of the finger. As used herein, dorsal in relation to a finger means that portion of the finger opposite the palm of the hand, and ventral means that portion of the finger adjacent the palm of the hand when a first is formed. The finger guide may also include a retentive or elastic layer that may function to hold the covering on a user's finger or thumb. The retentive layer may be located on a bottom of the covering, which fits over a ventral portion of the finger. The covering may be open-ended to allow a portion of a user's thumb or finger to extend through the covering. The portion of the user's thumb or finger that extends through the covering may allow the user to retain tactile sense while using the covering. The covering may be rotated during use to change the position of the protective surface.

Finger coverings and/or hand protectors may limit finger and/or hand flexibility of the user. Finger coverings and/or hand protectors may limit a user's sense of touch during a procedure. A user's sense of touch may be important during a medical procedure, especially if palpation of various surfaces of a treatment area is required during the procedure. A medical practitioner may need to retain a tactile sense during a medical procedure to control a patient and to maintain awareness of locations of sharp portions of instruments, inserts, and/or needles. Additionally, the use of finger and/or hand protectors may be limited by the amount of working space available within the patient. For example, a dentist does not have a large amount of working space within a patient's mouth. Also, a doctor typically does not have a large amount of working space within a patient during an invasive medical procedure.

SUMMARY OF THE INVENTION

In an embodiment, a protective glove for a hand, includes: a first thermoplastic layer; and a second thermoplastic layer heat welded to the first thermoplastic layer, wherein the second thermoplastic layer has a thickness greater than the thickness of the first thermoplastic layer.

In some embodiments, the first thermoplastic layer covers the palm of a user's hand during use and the second thermoplastic layer covers the back of the user's hand. In other embodiments, the first thermoplastic layer covers the back of a user's hand during use and the second thermoplastic layer covers the palm of the user's hand.

In an embodiment, the second thermoplastic layer has a thickness that is about twice the thickness of the first thermoplastic layer. The first thermoplastic layer may have a thickness of about between about 0.02 mm to about 1.0 mm or between about 0.1 mm to about 0.5 mm. The thickness of the second thermoplastic layer has a thickness that is greater than the thickness of the first thermoplastic layer and is in the range between about 0.1 mm to about 1.0 mm or between about 0.25 mm to about 0.75 mm.

In an embodiment, the first thermoplastic layer may have a durometer of about 20 A to about 100 A and the second thermoplastic layer may have a durometer of about 70 A to about 100 A or about 20 D to about 50 D. The second thermoplastic layer may be composed of two or more films heat welded together.

In an embodiment, the second thermoplastic layer may have a density that is greater than 1 g/cm³.

In some embodiments, first thermoplastic layer and/or the second thermoplastic layer comprises polyethylene or polyurethane. The first thermoplastic material and/or the second thermoplastic material may be formed from a material that is resistant to bodily fluids.

In an embodiment, the first thermoplastic material and/or the second thermoplastic material includes one or more folds which allow the first thermoplastic material and/or the second thermoplastic material to be bent without deformation of the first thermoplastic material and/or the second thermoplastic material.

In an embodiment, a guard for a digit of a hand, includes: a first thermoplastic layer; and a second thermoplastic layer welded to the first thermoplastic layer, wherein the second thermoplastic layer has a thickness greater than the thickness of the first thermoplastic layer.

In an embodiment, a method of making a protective glove, includes: placing a first thermoplastic film in contact with a second thermoplastic film, wherein the second thermoplastic layer has a thickness greater than the thickness of the first thermoplastic layer; heat welding the first thermoplastic film to the second thermoplastic film by placing a heated hand-shaped object in contact with the first thermoplastic film and/or the second thermoplastic film; and cutting the glove from the heat welded films.

In an embodiment, the hand-shaped object comprises a cutting edge which cuts the glove from the heat welded films when the hand shaped object is placed in contact with the first thermoplastic film and/or the second thermoplastic film. The hand-shaped object may be a planar object. During the process of making the glove, the hand-shaped object may be heated to a temperature above the glass transition temperature of the first thermoplastic film and/or the second thermoplastic film.

In an embodiment, a protective glove for a hand, includes: a first thermoplastic layer; and a second thermoplastic layer welded to the first thermoplastic layer, wherein the second thermoplastic layer has a durometer greater than the durometer of the first thermoplastic layer.

In some embodiments, the first thermoplastic layer covers the palm of a user's hand during use and the second thermoplastic layer covers the back of the user's hand. In other embodiments, the first thermoplastic layer covers the back of a user's hand during use and the second thermoplastic layer covers the palm of the user's hand.

The first thermoplastic layer may have a durometer of about 20 A to about 40 A and the second thermoplastic layer may have a durometer of about 70 A to about 120 A. The second thermoplastic layer may be composed of two or more films heat welded together.

In some embodiments, first thermoplastic layer and/or the second thermoplastic layer comprises polyethylene or polyurethane. The first thermoplastic material and/or the second thermoplastic material may be formed from a material that is resistant to bodily fluids.

In an embodiment, the first thermoplastic material and/or the second thermoplastic material includes one or more folds which allow the first thermoplastic material and/or the second thermoplastic material to be bent without deformation of the first thermoplastic material and/or the second thermoplastic material.

In an embodiment, a guard for a digit of a hand, includes: a first thermoplastic layer; and a second thermoplastic layer welded to the first thermoplastic layer, wherein the second thermoplastic layer has a durometer greater than the durometer of the first thermoplastic layer.

In an embodiment a method of making a protective glove, includes: placing a first thermoplastic film in contact with a second thermoplastic film, wherein the second thermoplastic layer has a durometer greater than the durometer of the first thermoplastic layer; heat welding the first thermoplastic film to the second thermoplastic film by placing a heated hand-shaped object in contact with the first thermoplastic film and/or the second thermoplastic film; and cutting the glove from the heat welded films.

In an embodiment, the hand-shaped object comprises a cutting edge which cuts the glove from the heat welded films when the hand shaped object is placed in contact with the first thermoplastic film and/or the second thermoplastic film. The hand-shaped object may be a planar object. During the process of making the glove, the hand-shaped object may be heated to a temperature above the glass transition temperature of the first thermoplastic film and/or the second thermoplastic film.

BRIEF DESCRIPTION OF THE DRAWINGS

Advantages of the present invention will become apparent to those skilled in the art with the benefit of the following detailed description of embodiments and upon reference to the accompanying drawings in which.

Figure 1A:
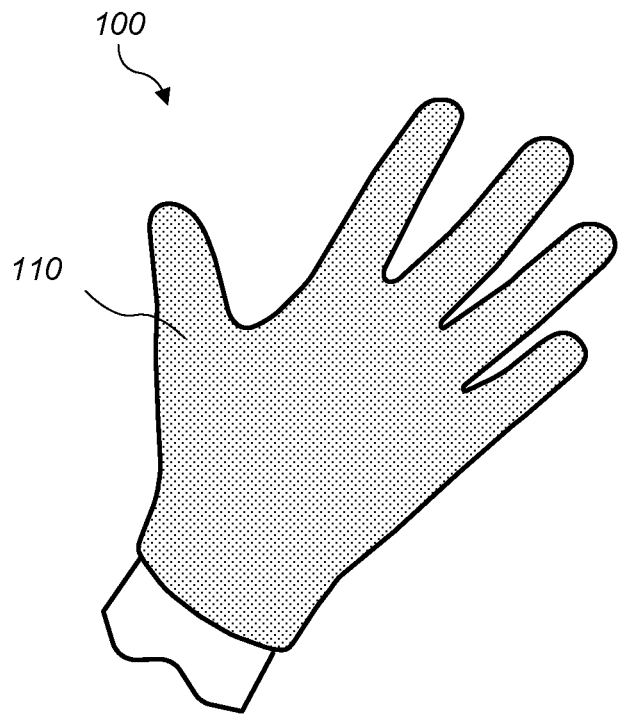
FIG. 1A depicts a puncture and/or cut resistant glove covering the back of a user's hand.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE INVENTION

A protective guard may include a flexible and penetration resistant construction to inhibit injury to a user's hands and/or fingers. As used herein the term "protective guard" refers to a protective glove, for the hand of a user, or a protective device for one or more digits of a hand. A digit, as used herein, may be a finger or a thumb. The protective guard may inhibit punctures or wounds caused by needles, knives, or other sharp instruments. For example, during the utilization of a mechanically engineered syringe, there is window of time before insertion and after withdrawal during which the needle tip is exposed. During this time, the protective guard may inhibit a medical practitioner from receiving an injury to a finger or thumb of the dominant or non-dominant hand while retracting, isolating, or stabilizing the needle tip.

In an embodiment, a protective glove for a hand includes: a first thermoplastic layer; and a second thermoplastic layer heat welded to the first thermoplastic layer, wherein the second thermoplastic layer has a thickness greater than the thickness of the first thermoplastic layer. In another embodiment, a protective guard for a digit of a hand includes: a first thermoplastic layer; and a second thermoplastic layer heat welded to the first thermoplastic layer, wherein the second thermoplastic layer has a thickness greater than the thickness of the first thermoplastic layer.

In an embodiment, a protective glove for a hand includes: a first thermoplastic layer; and a second thermoplastic layer heat welded to the first thermoplastic layer, wherein the second thermoplastic layer has a durometer greater than the durometer of the first thermoplastic layer. In another embodiment, a protective guard for a digit of a hand includes: a first thermoplastic layer; and a second thermoplastic layer heat welded to the first thermoplastic layer, wherein the second thermoplastic layer has a durometer greater than the durometer of the first thermoplastic layer.

In an embodiment, the first thermoplastic layer covers the palm of a user's hand during use, and the second thermoplastic layer covers the back of the user's hand. The second thermoplastic layer provides a penetration and puncture resistant material to the back of the user's hand. In such an embodiment, the second thermoplastic layer may also provide protection to the dorsal portion of the user's fingers. As used herein, dorsal, in relation to a finger, refers to the portion of the finger opposite the palm of the hand. As used herein, ventral, in relation to a finger refers to the portion of the finger adjacent the palm of the hand when a first is formed.

In an alternate embodiment, the second thermoplastic layer covers the palm of a user's hand during use, and the first thermoplastic layer covers the back of the user's hand. The second thermoplastic layer provides a penetration and puncture resistant material to the user's palm. In such an embodiment, the second thermoplastic layer may also provide protection to the ventral portion of the user's fingers.

The protective properties of the second thermoplastic layer are obtained by the increased thickness of the second thermoplastic layer with respect to the first thermoplastic layer. In some embodiments, the second thermoplastic layer has a thickness that is about twice the thickness of the first thermoplastic layer. In an embodiment, the first thermoplastic layer has a thickness of about between about 0.02 mm to about 1.0 mm, and wherein the thickness of the second thermoplastic layer is between about 0.1 mm to about 1.0 mm. In preferred embodiments, the first thermoplastic layer has a thickness of about between about 0.1 mm to about 0.5 mm, and wherein the thickness of the second thermoplastic layer is between about 0.25 mm to about 0.75 mm.

Alternatively, the first and second thermoplastic layers can be characterized by durometer measurements. In one embodiment, the first thermoplastic layer has a durometer of about 20 A to about 100 A, and the second thermoplastic layer has a durometer of about 70 A to about 100 A or about 20 D to about 50 D.

The first thermoplastic layer and the second thermoplastic layer may be formed from the same thermoplastic material or different thermoplastic materials. In one embodiment, the first thermoplastic layer and/or the second thermoplastic layer are made from a polyethylene polymer. Exemplary polyethylene that may be used for forming a protective guard for the hand include, but are not limited to: medium-density polyethylene (MDPE) having a density range of 0.926-0.940 g/cm$^3$; linear low-density polyethylene (LLDPE) having a density range of 0.915-0.925 g/cm$^3$; low-density polyethylene (LDPE) having a density range of 0.910-0.940 g/cm$^3$; very-low-density polyethylene (VLDPE) having a density range of 0.880-0.915 g/cm$^3$; high density polyethylene (HDPE) having a density range of 0.93-0.97 g/cm$^3$. In another embodiment, the first thermoplastic layer and/or the second thermoplastic layer are made from a polyurethane polymer. In some embodiments, the first thermoplastic layer may be formed from a polyethylene polymer, and the second thermoplastic layer may be formed from a polyurethane polymer.

It has been found that having a two layer glove, with the second thermoplastic layer having a thickness and/or durometer greater than the first thermoplastic layer improves the cut resistance of the glove. However, such gloves do not necessarily have improved puncture resistance. Further studies have shown that the density and/or the specific strength of the material can improve the puncture resistance. For example, using a polymer having a density greater than about 1.0 g/cm$^3$ improves the puncture resistance of the second thermoplastic layer. For example, polyurethane and polyvinyl chloride, when used as the material for the second thermoplastic layer showed substantial puncture resistance. Polyethylene having a density below 1.0 g/cm$^3$, while showing substantial cut resistance, showed very little puncture resistance.

In some embodiments, the material(s) used to form the protective guard are resistant to bodily fluids. Bodily fluids, are used herein, refers to fluids produced by a person including, but not limited to, blood serum, feces, mucus, saliva, sweat, tears, urine, and vomit.

The elastic properties of the thermoplastic materials used to form the glove may allow the hand, fingers and thumb to be bent or flexed. In some embodiments, a one or more folds may be formed in a portion of the protective guard to facilitate bending of the guard when the hand, finger or thumb is bent or flexed. The folds may allow the guard to conform to an anatomical shape of the hand, finger or thumb within the range of circumferences while the digit is bent or flexed. The first thermoplastic material and/or the second thermoplastic material may include one or more folds which allow the first thermoplastic material and/or the second thermoplastic material to be more readily bent. The folds may be positioned laterally (i.e., across the width of the fingers or back of the hand) or longitudinally (i.e., along the longitudinal axis of the fingers). Transverse folds may also be used to add flexibility to the protective guard. Folds may be positioned on either the ventral side or the dorsal side of the protective guard.

The color or colors of the protective portion of the protective guard may be different than the color of tissue and/or fluid (e.g., blood) to enhance view of the protective guard. In an embodiment, protective guards may be made in several sizes, with each size distinguished by a particular color. Such color coding may allow rapid visual differentiation between protective guard sizes. In other embodiments, protective material of a protective guard may be dyed a different color than less protective or retentive material of the protective guard. For example, the protective portion of a protective guard may be red, orange, yellow, green, or blue, while the less protective portion of the protective guard may be uncolored or skin colored. A portion of the protective guard may be made of a transparent or semi-transparent material. Alternatively, a protective portion of a protective guard may be painted or otherwise colored a different color than other portions of the protective guard. The color difference between the penetration resistant portion and the less penetration resistant portions of a protective guard may allow a medical practitioner to maintain awareness of the location of a protective portion of the guard during a medical procedure. The protective portion of a protective guard may be any color that contrasts with a user's skin and/or less protective section of the protective guard.

In an embodiment, a protective guard is made from FDA or USDA approved plastics and/or colors, such that the protective guard may be safely used in food preparation, including chopping, slicing, cutting, grating, dicing, paring, trimming, or mincing foods including, but not limited to, meats, vegetables, herbs, and fruits. In an embodiment, a surface of the protective guard may be used as a guide (e.g., as a guiding plane, allowing a knife or other instrument to glide smoothly along the surface while protecting a digit from cuts). Protective guards, as described herein, may also be used in other commercial fields where there is a chance of accidental puncture and/or cutting of a worker's hand. In some embodiments, the protective guard may be made from a biocompatible material for use in surgeries and other medical procedures.

The puncture/cut resistance of the second thermoplastic material may be compared to the puncture/cut resistance of a latex glove or a double layer of latex gloves. The puncture/cut resistance of a latex glove and/or a double layer of latex gloves may be the standard against which protection is compared. The resistance of the second thermoplastic material to penetration/puncture by a 27 gauge needle may be over four times greater than penetration resistance of a double layer of latex gloves, each glove having a thickness between about 0.05 millimeters and 0.2 millimeters. The penetration resistance of the second thermoplastic material to puncture by a 20 gauge needle may be over eight times greater than the penetration resistance of a double layer of latex gloves, each glove having a thickness between about 0.05 millimeters and 0.2 millimeters. In other embodiments, the penetration resistance of the second thermoplastic material to penetration/puncture by a 20 gauge needle may be over fifty-one times greater than the penetration resistance of a double layer of latex gloves, each glove having a thickness between about 0.05 millimeters and 0.2 millimeters.

Figure 1B:
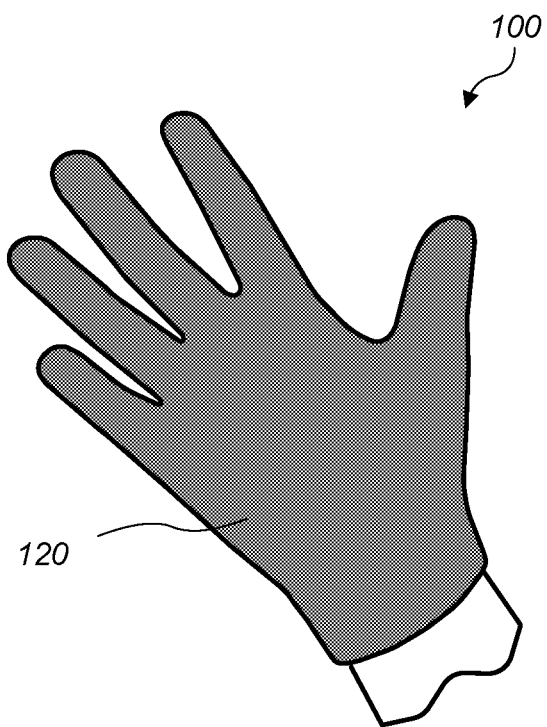
FIG. 1B depicts a puncture and/or cut resistant glove covering the palm of a user's hand.

Referring to the drawings and particularly to FIGS. 1A and 1B, a protective glove for a hand is designated by reference numeral 100. Protective glove 100 includes a first thermoplastic layer 110 and a second thermoplastic layer 120 that is welded to the first thermoplastic layer. Second thermoplastic layer 120 has a thickness greater than the thickness of the first thermoplastic layer 110. The second thermoplastic layer 120 inhibits a puncture or cut in the user's hands. The different colors used in the figures are meant to depict that the material on the palm side of the glove (FIG. 1B) has different properties then the material on the back side of the glove (FIG. 1A). The front and back sides of the gloves may be composed of materials having substantially the same color, or materials having different colors. The use of a first thermoplastic layer having a color that is different than the second thermoplastic layer may help the user identify the puncture/cut resistant side.

In some embodiments, the first thermoplastic layer 110 covers the palm of the user and the second thermoplastic layer covers the back of the user's hand. This combination provides protection to the back of the user's hands and fingers during use. In an alternate embodiment, the first thermoplastic layer 110 covers the back of the user and the second thermoplastic layer covers the palm of the user's hand. This alternate embodiment provides protection to the palm of the user's hands and fingers during use.

Medical practitioners may be, but are not limited to, doctors, physician assistants, nurses, dentists, dental assistants, oral surgeons, orthodontists, or oral hygienists. A medical procedure may include, but is not limited to, an invasive medical operation, a surgical reduction, a dental cleaning or procedure, an orthodontic procedure, insertion of a needle into a patient to inject or draw fluid, performing laboratory tests on tissue or fluid samples (including cases involving blood-borne pathogens and seroconversions), and cleaning or disposing of used instruments or needles.

Protective gloves and finger guards may be used to inhibit cutting or puncturing of skin by wires, knives, and other sharp or blunt instruments or objects, providing finger/thumb protection to workers including, but not limited to, jewelers, electricians, and carpenters. Protective gloves (and finger guards) may also be used in food preparation, electronics repair, and mechanical and engineering applications, such as space and aeronautical engineering applications. In some embodiments, protective gloves and finger guards may be used to provide first aid in situations involving cuts sustained on digits of a hand.

Material that forms the second thermoplastic layer may be dyed or painted a different color than the material that forms the first thermoplastic layer. In some embodiments, the color of the second thermoplastic layer may be a vivid color that results in a marked contrast with the color of the first thermoplastic layer. The color of the second thermoplastic layer may be chosen from, but is not limited to, FDA approved reds, oranges, yellows, greens, or blues. The color of the first thermoplastic layer may be the natural color of the material used to form the portion or any color that provides a noticeable contrast with the color of the second thermoplastic layer and/or a noticeable contrast with the color of a user's skin. The colors of the second thermoplastic layer and the first thermoplastic layer provide a contrast that allows a user (e.g. a medical practitioner) to distinguish between the two portions when the protective glove or guard is used.

Figure 2A:
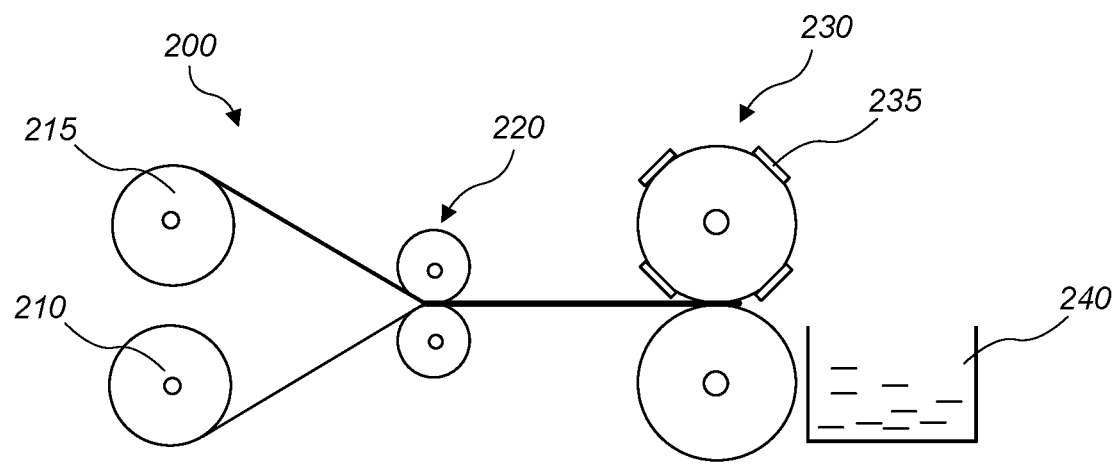
FIG. 2A depicts a schematic diagram of a heat welding apparatus.

In some embodiments, protective guards may be formed using a heat welding process. A schematic diagram of a heat welding apparatus 200 is depicted in FIG. 2A. As previously discussed, protective gloves and finger guards may be formed from a first thermoplastic layer heat welded to a second thermoplastic layer. A conveyor system, as depicted in FIG. 2A may be used to rapidly produce protective guards. A film composed of a first thermoplastic material may be supplied from a first supply reel 210. A film composed of a second thermoplastic material may be supplied from a second supply reel 215. The second thermoplastic film has a thickness that is greater than the thickness of the first thermoplastic film.

The first thermoplastic film and the second thermoplastic film are carried through the heat welding apparatus by combining wheels 220 and heat welding system 230. Combining wheels 220 are formed from substantially cylindrical wheels which force the first thermoplastic layer and the second thermoplastic layer into contact with each other. The resulting combined film is transferred to heat welding system 230.

Figure 2B:
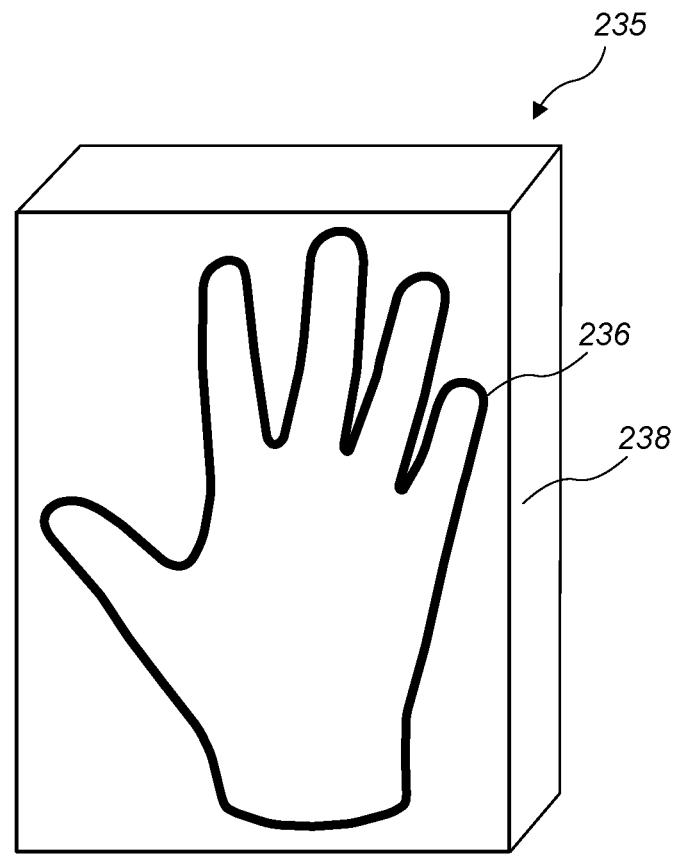
FIG. 2B depicts a schematic diagram of a cutting and heat welding die.

The combined film is then passed through welding system 230 which includes one or more cutting and heat welding dies 235. An expanded view of a cutting and heat welding die 235 is depicted in FIG. 2B. A cutting and heat welding dies 235 includes a die 236 in the outline of the protective guard being formed (e.g., a glove) and a body 238. Die 236 and body 238 are formed from a material (e.g., a metal such as steel or aluminum) that can be heated above the glass transition temperature of the first thermoplastic layer and/or the second thermoplastic layer. Die 236 may include sharpened edges that are capable of cutting the combined film.

During production, the heated die 236 welds the first thermoplastic film to the second thermoplastic film at the outer boundary of the protective guard. The produced protective guard may be collected in collection bin 240.

It should be understood that while depicted as being used to form a protective glove, heat welding apparatus 200 may be used to prepare finger guards. In a modification of the heat welding apparatus, the combined film, formed from the first thermoplastic layer and the second thermoplastic layer, may be produced separately and provided to welding system 230 directly from a supply reel.

Other methods may be used to produce the gloves. Such methods include radio frequency welding, sonic welding, and any other class of polymeric welding.

EXAMPLES

Three materials were tested for cut resistance and puncture resistance. The materials tested included Sample 1-90 A polyethylene, 0.5 mm; Sample 2-90 A, polyethylene, 0.25 mm; Sample 3-70 A polyethylene, 0.125 mm. Samples 1 and 2 represent the second thermoplastic layer of a glove, while Sample 3 represents the first thermoplastic layer of the glove. Shown below in Table 1 are the results of the tests.

| Sample | EN 388 6.5 Puncture resistance | ANSI/ISEA 105-2016 5.1.1 Cut Resistance | ANSI/ISEA 105-2016 5.1.3 Puncture Resistance |
| --- | --- | --- | --- |
| Sample 1 | Level 0 | Level A2 | Level 0 |
| Sample 2 | Level 0 | Level A2 | Level 0 |
| Sample 3 | Level 0 | Level A1 | Level 0 |

For the EN 388 puncture resistance tests, Level 0 corresponds to a puncture occurring under less than 20 N. For the ANSI puncture resistance test, Level 0 corresponds to a puncture resistance of less than 2N. For cut resistance testing, Level A1 is ≥200 g, Level A2 is ≥500 g. Thus, Samples 1 and 2 offer a significant improvement over the base layer (Sample 3).

In this patent, certain U.S. patents, U.S. patent applications, and/or other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A protective glove for a hand, comprising:
   a first thermoplastic layer in the shape of a hand; and
   a second thermoplastic layer, in the shape of the hand, welded to the first thermoplastic layer, wherein the second thermoplastic layer has a durometer greater than the durometer of the first thermoplastic layer; and wherein the second thermoplastic layer has a thickness between about 0.1 mm and about 1.0 mm, and wherein the second thermoplastic layer is composed of a polyethylene film;
   wherein the first thermoplastic layer is welded to the second thermoplastic layer to form a glove for a hand,
   wherein an opening exists between the first thermoplastic layer and the second thermoplastic layer which allows a user to place their hand into the glove, such that the user's hand is between the first thermoplastic layer and the second thermoplastic layer.

2. The protective glove of claim 1, wherein the first thermoplastic layer covers the palm of a user's hand during use, and wherein the second thermoplastic layer covers the back of the user's hand.

3. The protective glove of claim 1, wherein the first thermoplastic layer covers the back of a user's hand during use, and wherein the second thermoplastic layer covers the palm of the user's hand.

4. The protective glove of claim 1, wherein the first thermoplastic layer has a durometer of about 20A to about 100A, and wherein the second thermoplastic layer has a durometer of about 70A to about 100A.

5. The protective glove of claim 1, wherein the second thermoplastic layer is composed of two or more films heat welded together.

6. The protective glove of claim 1, wherein the first thermoplastic layer is composed of a polyethylene film.

7. The protective glove of claim 1, wherein the first thermoplastic material and/or the second thermoplastic material comprises one or more folds which allow the first thermoplastic material and/or the second thermoplastic material to be bent without deformation of the first thermoplastic material and/or the second thermoplastic material.

8. The protective glove of claim 1, wherein the first thermoplastic material and/or the second thermoplastic material is resistant to bodily fluids.

9. The protective glove of claim 1, wherein the second thermoplastic layer is a different color than the first thermoplastic layer.

* * * * *